United States Patent [19]
Reydel et al.

[11] Patent Number: 5,259,366
[45] Date of Patent: Nov. 9, 1993

[54] METHOD OF USING A CATHETER-SLEEVE ASSEMBLY FOR AN ENDOSCOPE

[76] Inventors: Boris Reydel, West Tenn. Medical Specialty Clinic, 534 Roland Ave., Jackson, Tenn. 38301; Iosif Galperin, 2903 Fallstaff Rd. #302, Baltimore, Md. 21209

[21] Appl. No.: 970,833

[22] Filed: Nov. 3, 1992

[51] Int. Cl.$^5$ .............................................. A61B 1/00
[52] U.S. Cl. ......................................... 128/4; 604/102; 363/203
[58] Field of Search ............... 128/4; 606/110, 113, 606/114, 139, 143; 604/102, 160, 161; 383/97, 203

[56] References Cited

U.S. PATENT DOCUMENTS

| | | | |
|---|---|---|---|
| 4,285,376 | 8/1981 | Ausnit | 383/203 X |
| 4,646,722 | 3/1987 | Silverstein et al. | |
| 4,741,326 | 5/1988 | Sidall et al. | |
| 4,886,049 | 12/1989 | Darras | 128/4 |
| 5,025,778 | 6/1991 | Silverstein et al. | 128/4 |
| 5,100,420 | 3/1992 | Green et al. | 128/4 X |
| 5,171,222 | 12/1992 | Euteneuer et al. | 604/102 |

OTHER PUBLICATIONS

C. Paul Swain et al., "An endoscopic stapling device: the development of a new flexible endoscopically controlled device for placing multiple transmural staples in gastrointestinal tissue", *Gastrointestinal Endoscopy*, vol. 35, No. 4, 1989, pp. 338 and 339.

C. Paul Swain et al., "An endoscopic sewing machine" *Gastrointestinal Endoscopy*, vol. 32, No. 1, 1986, pp. 36–38.

*Primary Examiner*—Richard J. Apley
*Assistant Examiner*—Beverly A. Meindl
*Attorney, Agent, or Firm*—Laurence R. Brown

[57] ABSTRACT

A catheter sleeve assembly with a zipper-like locking structure is positioned on the outer cylindrical surface of an endoscope at a position outside the body while the endoscope is in viewing position inside the body. The zipper-like locking structure is split and the catheter-sleeve assembly is positioned about the endoscope body and locked into place. The catheter-sleeve assembly is then shuttled into and out of the distal viewing site along the body of the endoscope by manual manipulation while the endoscope remains in viewing position. Surgical stapling and tissue removal procedures can be performed with endoscopic surgical instruments passed down a lumen provided in the catheter-sleeve assembly.

3 Claims, 4 Drawing Sheets

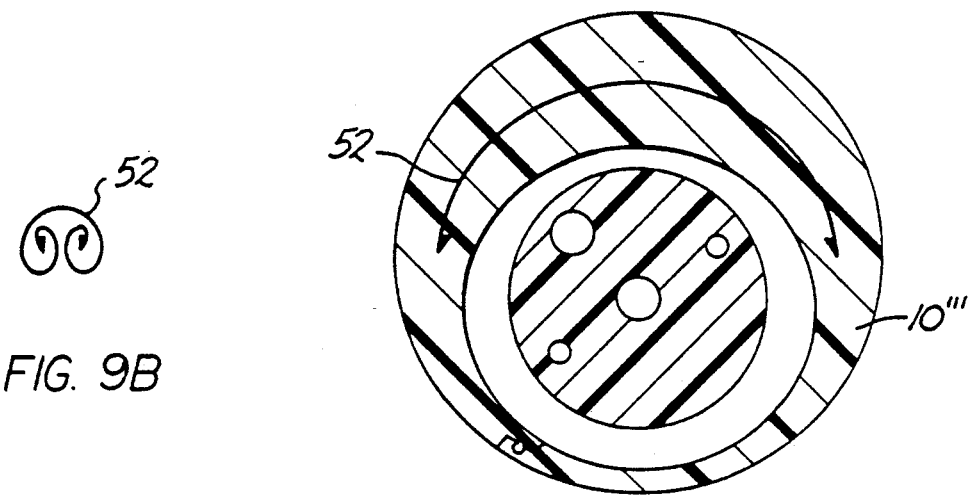
FIG. 9B
FIG. 9A
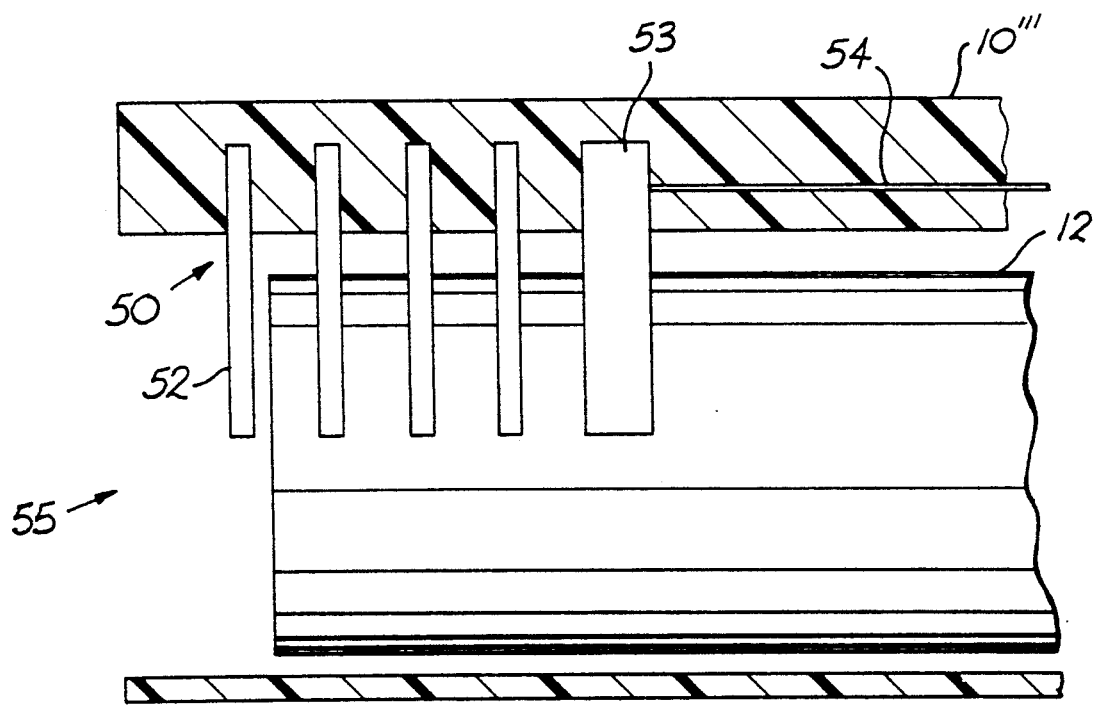
FIG. 9C

METHOD OF USING A CATHETER-SLEEVE ASSEMBLY FOR AN ENDOSCOPE

TECHNICAL FIELD

This invention relates to endoscopy and more particularly it relates to surgical methods and apparatus for surgical treatment within body channels employing endoscopes.

BACKGROUND

The use of endoscopes for diagnostic and therapeutic treatment is rapidly expanding. To improve performance, endoscopes have been optimized to best accomplish their purpose. For instance, there are "bleederscopes" with one large or two smaller operative channels to ease high-volume suction and/or conveying to the viewing site a therapeutic catheter (i.e. electrocautery, polypectomy snare, laser optic fiber, biliary stent, gallstone basket, etc.)

The size of the therapeutic catheter is inherently predetermined by the size of the operative channel of the endoscope. Some of the therapeutic catheters can change their size as soon as they passed through the scope and come out from the distal end of the scope into the operative field. Polyp-grasper catheter, wall stent biliary stent, gallstone basket are some of the examples. Large size (compared to the size of the regular operative channel which is 3.2 mm) subjects of interest could be held by above mentioned catheters in front of the distal end of the scope but they cannot be removed or introduced through the operative channel of the scope which is frequently the case (i.e. a piece of the polyp, a gallstone, a foreign object, or a stent, etc.) In such cases, usually the subject of interest is held by the "grasping part" of the operative catheter in front of the distal part of the scope after which the whole complex of endoscope, plus catheter plus subject of interest is withdrawn from the body. A great deal of time is lost for example in the case of right colonic polyp/polyps since for every polyp removal the scope is removed and reintroduced to the site of the polypectomy through the entire, sometime very tortuous colon (1.5 meter long), or to check for the absence of bleeding from the site/- sites of the polypectomy.

The size of the operative channel of the endoscope has become a dominant and simultaneously limiting factor in the expanding of the boundaries of the therapeutic endoscopy in existing and potentially new techniques. For instance, suturing or stapling through the flexible endoscope is still in its infancy.

For the laparoscopy there is a stapling device described in any textbook for laparoscopic cholecystectomy, but it staples ducts or vessels by being applied to the external surfaces of those structures and device itself is not flexible.

For the flexible endoscopy there were publications of the experimental stapling (by C. P. Swain et al. in Gastrointestinal Endoscopy, 1989, 35(4), p. 338-339) or sewing devices (by C. P. Swain et al. in Gastrointestinal Endoscopy, 1986, 32(1), p.36-38). Those devices have to be mounted on the distal end of the scope before its insertion into the body. Both of those devices inevitably obstruct the front view and the whole introduction of such complexes would have to be performed through an overtube as a protective sheath, preinserted inside the hollow organ. The overtube itself has its own limitations (due to its relative rigidity it could not be passed into the small intestine or deep into the colon).

The other device used with flexible endoscope is the one applied for the ligation of the esophageal varices with resin bands (BARD Company product, procedure described in common textbook). In that case, cylinders with bands also have to be mounted on the distal tip of the scope before introduction into the body. One can apply only one band at a time so that the scope has to be withdrawn every time for remounting a new band at the endoscopic tip. An overtube has to be used for multiple reinsertion of the scope, which could be traumatic.

There are no known stapling/sewing or banding devices that could be delivered to the operative field through the operative channel of the scope.

In the endoscopy field, different types of the "overtubes" or endoscopic sheaths have been described. U.S. Pat. No. 4,646,722 (by F. E. Silverstein, et al.) described a protective disposable endoscopic sheath which is applied over the external surface of the flexible endoscope to prevent contamination of the scope with fecal bacteria and perhaps to avoid costly disinfection. This sheath has to be introduced over the scope like a "stocking" from its distal end up before the procedure starts, that is when the scope is outside the body.

Similar protective disposable sheaths are described in U.S. Pat. No. 4,741,326 (by C. O. R. Sidall, et al.) which also must be installed over the scope from its distal end before the procedure starts.

There is an overtube commonly used in endoscopy to remove a foreign body from the intestine or stomach (particularly, when foreign object has sharp ends, i.e. safety pin). That overtube is described in any endoscopy textbook. Usually it is a tube, only slightly flexible, with the diameter larger than the one of the endoscope, which is pre-inserted over the external surface of the endoscope and held over the proximal end of the endoscope while its distal end is being inserted into the hollow organ and advanced to the depth of interest. Then an overtube is slid over the external surface of the endoscope. Then the endoscope, with the sharp object being held in front of its distal end (since it cannot be retracted inside the small operative channel) is withdrawn inside the overtube. Thus, the overtube protects the pulmonary system and esophagus as a protective sheath.

There are multiple overtubes of different shape, length and flexibility (there is even one with small operative channel inside its wall, described by S. Kitano in British Journal of Surgery, 1987, 74, p. 603-606). However, there is a common denominator for all of them that is all of them are cylindrical tubes that have to be inserted over the external surface of the endoscope from its distal end, when the scope is outside the body. So the operator must know in advance that he is going to need one and pre-insert it over the scope before starting the procedure. Thus, the scope would have to be withdrawn and reinserted should the need for overtube occur (increasing the risk of potential complications as well as making the procedure lengthy and somewhat cumbersome).

It is an object of this invention to improve this state of the art by providing improved protective sheath structure.

It is a further object of the invention to create a new family of the catheters for flexible endoscopes that traverse not through the internal operative channel of the scope, but rather over its external surface. As a regular "internal" catheter the external catheter could be used in the middle of ongoing procedure without having to withdraw the scope for assembly, as it is a case with commonly used overtubes.

SUMMARY OF THE INVENTION

In accordance with this invention, the catheter cylindrical tube overlies the endoscope portion outside a body cavity by means of a longitudinal gap through its length in the manner of a removable bracelet. Much like a plastic "zipper", the external catheter may be "snapped" onto the part of the endoscope which stays outside the body (proximal part of the endoscope next to the operative head of the scope). Then, the "external" catheter is slid over the surface of the scope inside the body to the distal working end.

After the catheter gap is spread open and "snapped" onto the scope, the longitudinal incision may be re-sealed like a zipper. Thus, the catheter embraces the external circumference of the scope completely, which will assure that the catheter follows exactly the course of the endoscope inside the hollow organ and will not "snap off" at the points of its acute angulation.

Due to the fact that the external catheter travels over the external surface of the scope, its diameter due to wall thicknesses is limited only by the diameter of the lumen of the hollow organ. Thus, large-size objects (polyps, gallstones, stents) may be delivered or withdrawn in and out of hollow organs. A large bore channel or several channels may be disposed over the outside surface of the scope enabling the operator using a regular scope to accomplish several functions simultaneously (lifting-and-cutting; using laser and suction at the same time etc.).

The fact that the size of the external catheters of this invention are limited only by the diameter of lumen of the hollow organ, opens a new horizon for stapling-/sewing/band-ligation devices, and the like. For example, stapling devices may utilize the external catheter as a delivering system.

Stainless steel staples have a U-shape when free. In a ready-to-go position staples straighten out on the rectangular plate which serves as a cartridge. If they are pushed off that plate, the staples would immediately re-assume their U-shape, that is two ends of the staple would come close to each other and "pinch any tissue lying in between them. If the plate with "ready-to-go" staples on it is slightly pressed against mucosa (i.e. gastric mucosa) and the first staple pushed off the plate, its two ends will "pinch" the tissue that lies between them. The rectangular plate-cartridge with staple is inserted inside a nitch or "cave" at the distal end of the external catheter. Inside the wall of that catheter, there is a channel through which a small manipulative tube comes to a proximal end of the plate-cartridge and gets screwed onto it. That small tube, when screwed into the cartridge pushes it out of the nitch into the operative field. By rotating the small tube, the rectangular plate could be brought into the direct contact with diseased mucosa. Inside the manipulative tube there is a smaller wire which is attached to a "pusher" that pushes staples out of a stored set in a controlled manner, one after another as needed.

Another possible therapeutic device that could be installed within the wall of external catheter is "multistaple ligation device". A row of semicircular resilient staples (made from polymer or metal) are positioned inside the wall of the distal end of the proposed catheter. When, say esophageal varices are discovered during diagnostic EGD, the above mentioned tube could be slid over the external surface of the regular endoscope. The distal end of the catheter is extended two-thirds of a cm in front of the distal tip of the scope. The varix is suctioned into the space between the distal ends of the catheter and scope. The "pusher", which is located behind the row of staples, pushes them till the first staple is off. When it is off, its ends coil inside on themself assuming a "double-spiral" shape, thus strangling the base of the varix. This procedure is repeated as needed without having to withdraw the scope of reloading as is necessary in current techniques.

BRIEF DESCRIPTION OF THE DRAWINGS

In the accompanying drawings, wherein like reference characters relate to similar features in the different views to facilitate comparison,:

FIGS. 9A, 9B and 9C are respectively an end view of an endoscope-sheath embodiment of the invention for inserting surgical staples ready to release in-situ for ligation of varices, the configuration of a released staple, and a side view sketch of an external catheter embodiment of the invention for multiple ligation of varices disposed at the distal end of the endoscope for release of the staples.

THE PREFERRED EMBODIMENTS

This invention provides a new family of the multi-functional catheters that are passed externally to the body over a flexible endoscope and slid there over into the body to a work site.

Figure 1:
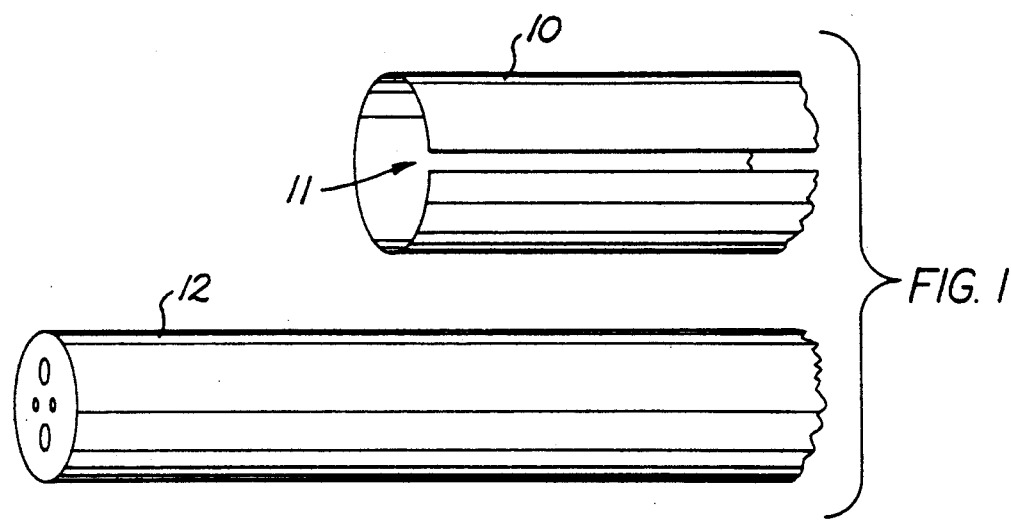
FIG. 1 is an exploded view of an endoscope and after-insertion sheath mount embodiment of the invention.

The catheter sheaths 10 of FIG. 1 thus have a gap 11 for spreading to snap the cylindrical sheath over endoscope body 12. Thus, the sheaths 10 may be introduced inside the body into the operative field right in the middle of the regular endoscopic procedure without having to withdraw the endoscope.

The catheter sheath 10 comprises a tube with internal diameter equalling or slightly exceeding the external diameter of the endoscope 12. The tube 10 has a longitudinal slit 11 thus creating an incomplete bracelet like cylinder in this embodiment. During the endoscopy procedure the distal part of the endoscope is inserted inside the hollow organ and protruding from the body there is an external part of the endoscope with regulatory handle (not shown).

Figure 2:
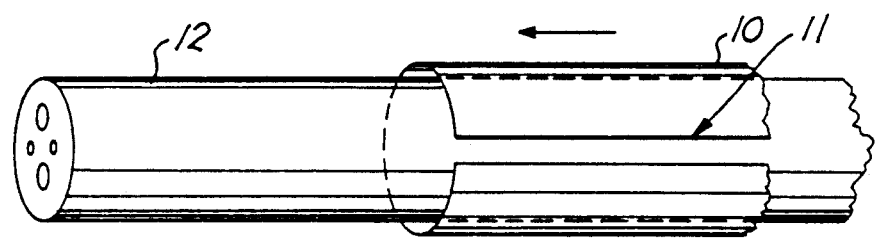
FIG. 2 is an assembled view of the endoscope and sheath of FIG. 1.

Should the need for a catheter occur, the bracelet-like incomplete-cylinder catheter 10 is spread and snapped onto the part of the scope 12 which is located outside the body, close to the regulatory handle (proximal part of the scope). Then, using the endoscope body as a guidance rail the external bracelet-like catheter 10 may be slid inside the body/hollow organ and advanced to the distal end of the scope 12, right to the operative visual field where catheter's function is required (FIG. 2).

Figure 4:
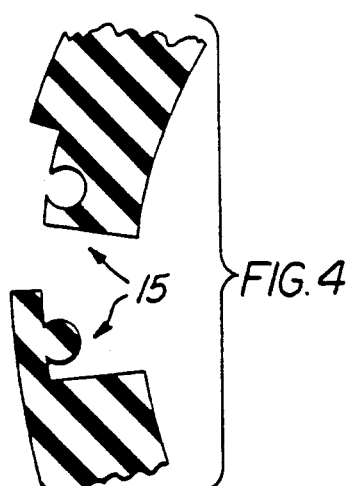
FIG. 4 is an enlarged fragmental view in section of a "zipper" type sheath closure embodiment or the invention.
Figure 3:
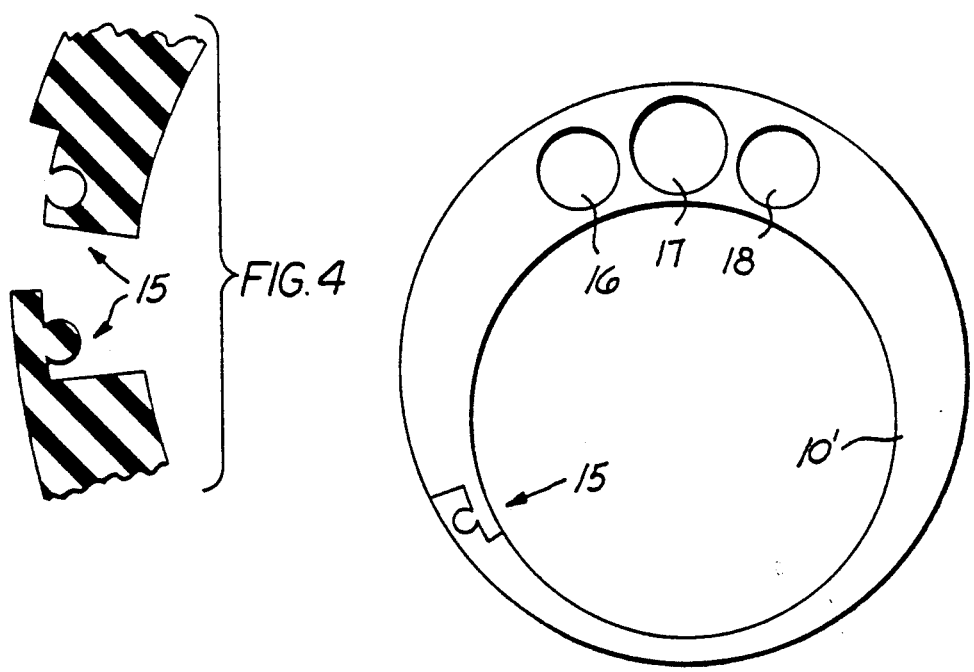
FIG. 3 is a distal view of a sheath embodiment of the invention.

To avoid divergence of the external catheter from the flexible endoscope at the points of acute angulation inside the hollow organ, the "completeness" of the external catheter-cylinder is restored as soon the catheter is snapped onto the proximal part of the scope outside. In FIGS. 3 and 4, a "zipper" configuration 15 of the ends of the longitudinal slit along the catheter cylinder length locks the tubing about the catheter body (FIG. 3).

Thus, as soon as the bracelet-catheter cylinder is secured over the external part of the endoscope, it may easily be threaded over the external surface of the flexible endoscope to its distal part inside the body, almost like a stocking. Then, the lumens 16, 17, 18 in the catheter 10' wall permit entry of tubes and instruments into the endoscope viewing region.

Figure 5A:
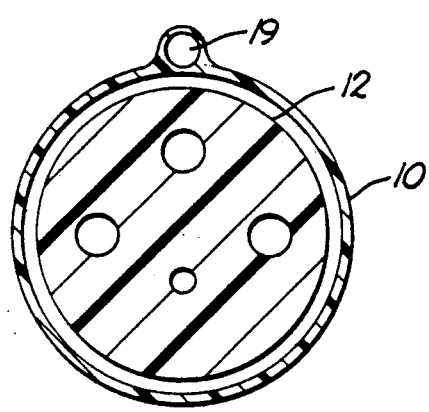
FIGS. 5A and 5B are further embodiments in end view of the assembled catheter-sheath assemblies such as shown in FIG. 2.
Figure 5B:
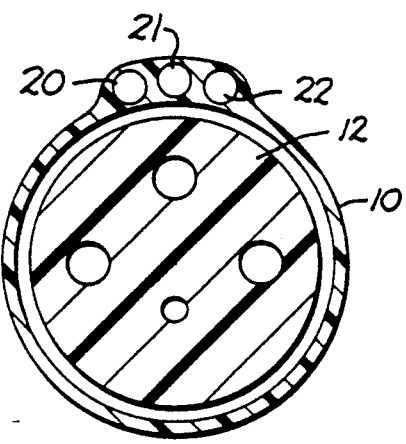

The catheter itself is made from the very flexible material (synthetic polymer, i.e. silicone) which could be easily molded or extended into the needed structure (extrusion technique is commonly used for multichannel tubes). The wall of the catheter will be very thin all around, except for a working sector (FIG. 5A, B). That part of the catheter's perimeter will carry the "working devices" depending on the purpose of that particular bracelet-catheter. For instance, it may contain one 19 or several 20, 21, 22, channels (FIG. 5A, B). By using the catheter of FIG. 5A or B, the operator will create 1 or 3 additional channels along the external surface of the flexible endoscope. Thus, one may simultaneously pass, say cautery, laser and suctioning catheters to save time, making a procedure shorter, more efficient and less traumatic. (The operator thereby does not have to withdraw the regular endoscope and reinsert a "double-channel bleeder" scope). Alternatively, the catheter 10 may have one large-bore channel to deliver to or remove from the operative field a large-size object (stone, blood clot, stent, etc.).

Figure 6:
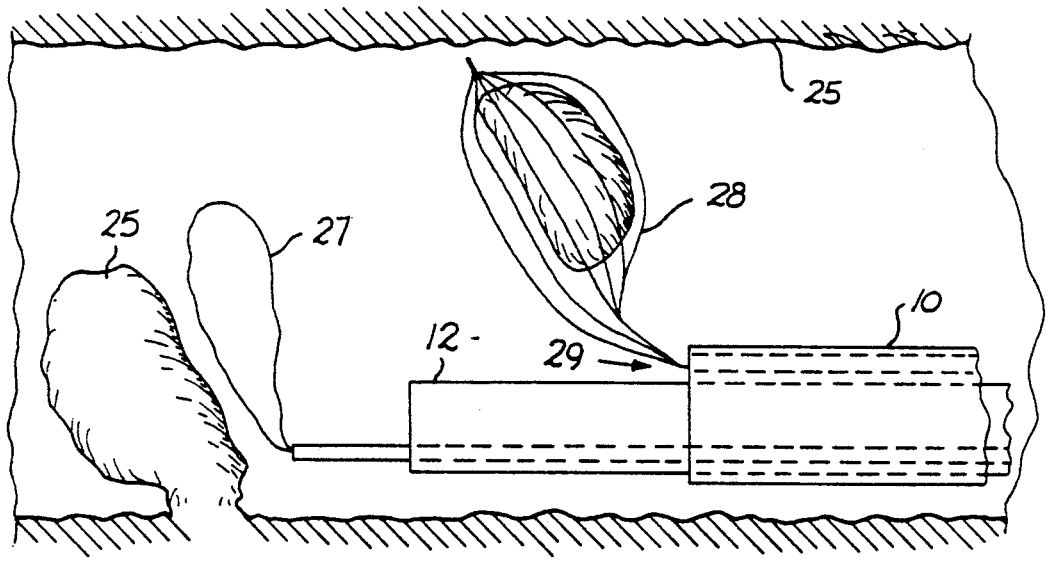
FIG. 6 is a diagrammatic view of an endoscope apparatus embodiment of the invention in-situ at a surgical treatment site in the colon for removing and retrieving polyps.

The other possible implication of external catheters is that they could function as a shuttle to withdraw really large objects such as large polyp (or pieces of the polyp) as sketched in FIG. 6 without having to withdraw the whole endoscope, which heretofore is the only currently existing method. In the case of polypectomy in the right colon 25 having a polyp 26 to be removed by snare 27, a basket 28 is manipulated through lumen 29 in catheter 10 riding on endoscope 12 to gather and remove the severed polyp. Heretofore, when the scope with polyp is being withdrawn and the scope must be reintroduced into the right colon, and the endoscopist has no visual control of the polypectomy site. That is not the case when external shuttle-catheter 10 is slid in or out of the body over the scope 12 which stays all the time right at the site of the polypectomy to monitor bleeding.

It is possible because the only limiting factor for the size of the external catheter is the narrowest point of the hollow organ 25 (anus or colonic stricture for the colon or pharynx/esophageal stricture for the upper endoscopy). In other words, the distal end of the endoscope during the entire length of the endoscopic procedure stays in the operative field giving the operator an absolute visual control of the operative condition inside the organ while anything needed could be delivered or withdrawn along the external surface of the endoscope.

Clearly, the variety of the bracelet-catheters is essentially unlimited. All types of currently existing catheter implements may be passed over the channel/channels, or may be built-in within its wall. Moreover, different purpose catheter devices could be passed simultaneously.

Figure 7A:
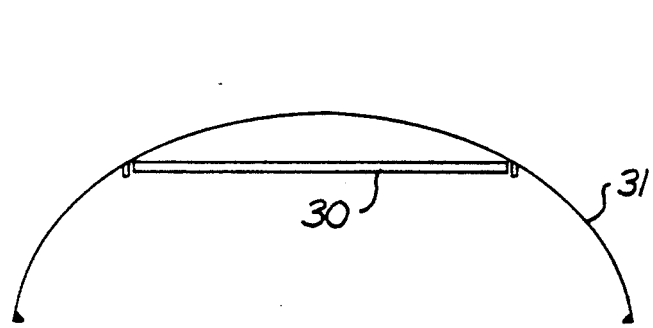
FIGS. 7A and 7B are respectively end views representing surgical staples as disposed on a carrying plate and as released in a tissue clamping posture.
Figure 7B:
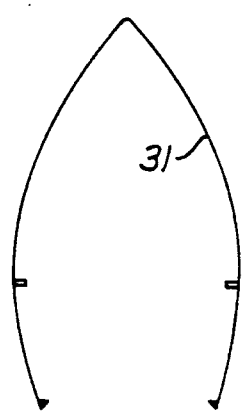
Figure 8A:
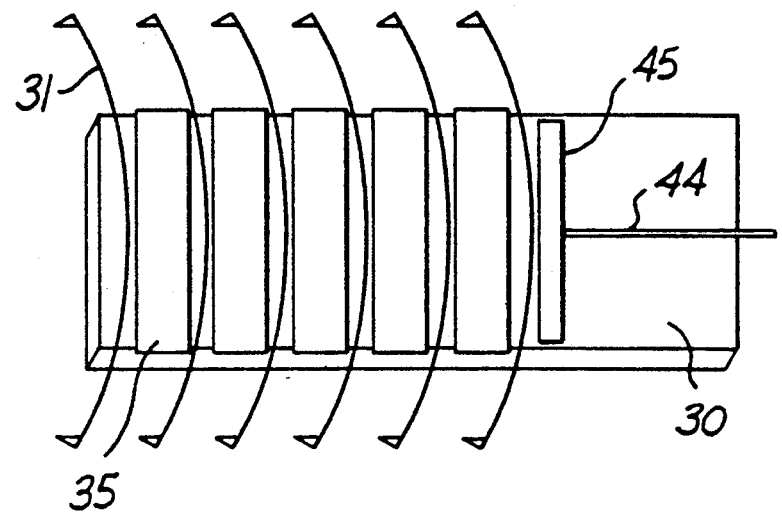
FIGS. 8A and 8B are respectively side view sketches in section of a rack of surgical staples ready for dispensing and of an endoscope fitted with a staple dispensing sheath for positioning in-situ at a surgical site being observed by the endoscope.

Again, since the only limiting factor for the size is the narrowest point of the lumen of the organ to be examined, relatively large devices could be delivered to the operative field. For instance, a bracelet-catheter 10 functioning as a shuttle could deliver a multi-staple stapling device. Thus, several stainless staples 31 are mounted onto the rectangular plate 30, FIG. 7A. Each staple when free has an "inborn" memory-shape, namely U-shape (FIG. 7B). If the staple is pushed off the plate, it goes from the "sector-shape" into the "U-shape" configuration. When it assumes the "U-shape" it pinches whatever tissue was interpositioned between two ends of the "sector". The "U-shape" staples are stretched out onto the rectangular plate in a ready-to-go "sector-shape". Behind the row of staples, there is a pusher attached to the wire which when advanced forward pushes the staples off one by one in a controlled fashion (FIG. 8A). Staples could be interpositioned with small "bricks" 35 made from the material that could be dissolved within the lumen of the intestine (say soluble fibers). Those "bricks" will separate two staples to simplify their controlled release.

Figure 8B:
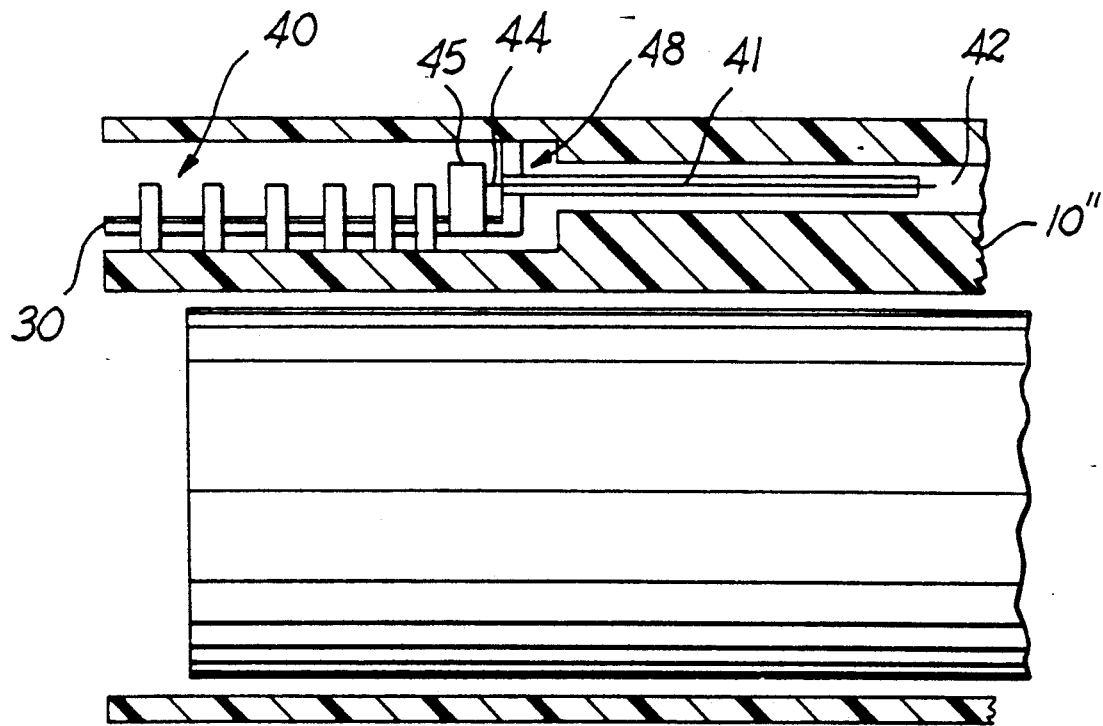

The rectangular plate with staples and pusher on it is hidden inside the nitch 40 within the wall of the distal end of the external bracelet-catheter 10 of FIG. 8B. A thin manipulatory tube 41 (i.e. 1 mm in diameter) attached to the rectangular plate 30 goes within the lumen 42 of the catheter 10'. When manipulatory tube 41 is pushed forward the rectangular plate comes out of the nitch into the operative field and there may be rotated and manipulated to come into direct contact with for example a gastric wall which has a bleeding tear, or base of the polyp. The ends of the ready-to-go "sector-shape" first staple 31 are abutted against the mucosal tear (bleeding ulcer, vessel, base of the polyp, etc.). Then the pusher wire 44 which goes through the manipulatory tube, advances pusher 45 which, in turn pushes the staple 30 off to pinch the tear and close it off. Then, the plate 30 is manipulated a bit and another staple is ready to come off at another location (i.e. to close the tear further, etc). The pusher-wire 44 which goes inside the manipulatory tube 41 is threaded with a pitch. Thus, for example, every two full turns of the pusher-wire outside the body will advance the pusher 45 over the rectangular plate 30 a precise distance. That will be exactly the distance to push just one staple 31 off the plate 30. The plate 30 with staples 31 could be disposable and used as a "cartridge" which is screwed onto the manipulatory tube at 48. The specific bracelet-catheter 10" for stapling with the nitch 40 at its distal end and manipulatory tube 41 with pusher-wire 44 inside could be a reusable device.

The external catheter 10 also may be used for a procedure similar to currently existing variceal band ligation. The well-known rubber band ligation technique is described briefly. A small plastic cylinder with a single rubber band stretched on its perimeter is mounted on the distal end of the endoscope before it is introduced into the esophagus. Then scope is inserted and the distal tip of the scope is abutted against the varix, which moves into the cylinder. A release-wire releases the rubber band to strangle the base of the varix. Then to ligate another varix, the operator must withdraw the scope, take off the used cylinder, mount a new one with a new rubber band on it and the scope must be reinserted. Due to multiple passages, an overtube should be introduced before the procedure is started to prevent pharyngeal tradma and aspiration. The internal operative channel of the endoscope is occupied with the "release-wire" so the suctioning during the procedure is really inefficient.

The external catheter 10''' is specialized for simultaneous multiple ligation of the varices, FIG. 9. A row 50 of semicircular stainless or plastic polymer staples 52 is inserted inside the wall of the distal end of the external catheter 10''' which is attached to the pushing wire or thin tube 54. Thus, two turns of the wire/tube will push just one staple 52 off the distal end, FIG. 9B, of the external catheter. When staple is off the catheter, it assumes its built-in shape. The ends of the semicircular staple will coil on themselves inwardly like two spiral springs. Now, when an endoscopist diagnoses a varices during the procedure, he does not have to withdraw the scope to introduce a protective overtube and mount a plastic cylinder with a single rubber band to perform ligation. All he has to do to snap a specialized external catheter onto the portion of the scope which is outside the body, zip-lock it to mount the cylinder and thread it inside the body along the external surface of the scope. Then external catheter 10''' is advanced slightly distally to the tip of the scope. The varix is positioned into the tubular mouth 55 of the catheter. The pusher wire/tube 54 is rotated two full turns to push the first staple off the catheter 10''' an it strangles the base of the varix. A built-in spiral-spring force the strangles the base of the varix, continuing for several days while it is being deprived of blood supply and varix eventually dissolves. Then the tip is manipulated to another varix which is strangled in a similar fashion. When strangled the varix will dissolve inside the intestinal lumen together with the staple. And that is where the "two-spiral shape" of the staple is particularly advantageous to prevent traumatization of the intestinal wall. Instead of being sharp-pointed the points will coil inside on themself. By doing that, the staple will also decrease in size to 3-4 mm, which will also prevent any possibility of intestinal obstruction.

It is of interest that in this procedure the external catheter 10'' will simultaneously function as an overtube protecting from aspiration of blood in acute bleeding. The creation of the external catheter 10''' also leaves the internal operative channel of the scope free for observing and completing more precise manipulations.

The essence of the proposed invention is to use the external surface of the flexible endoscope to create new tooling converting the regular endoscope into multi-channel, multipurpose therapeutic device. By using a "bracelet-like" structure of the catheter, one is able to snap it onto external surface of the scope at any point of its length and slide it inside the body. It could also function as a shuttle to deliver to or withdraw from the hollow organ large size objects which would be impossible to move through the internal channel of currently existing scopes. It makes surgical procedures much shorter in duration, more efficient and safe since the operator does not lose visual control at any time. It is also of interest that much smaller caliber scopes could be used with that small caliber scope being converted when necessary into a "large-channel or multi-channel" scope. Because the limiting factor for the size of the external catheter is only the lumen diameter of the hollow organ to be examined, a "multistaple-stapling or varix-strangulated" devices could be delivered over the regular common endoscope without having to interrupt the procedure.

Thus a catheter system is provided by this invention with a deformable catheter-sleeve cylinder member that retains a cylindrical shape of a diameter for fitting about the outer cylindrical surface of an endoscope, with an inner surface that slides along the outer surface of the endoscope, and provided with a longitudinal gap along the cylinder for spreading open the cylindrical sleeve to force the sleeve member over the endoscope outer surface at a position outside the body without removing the endoscope from an observation position within a body opening. The retained cylindrical shape mates in a sliding relationship with the endoscope outer surface so that it can be moved to the surgical site at the distal end without disturbing the continual viewing of the site by the endoscope.

This invention makes possible for the first time an endoscopic treatment method wherein an endoscope with a substantially cylindrical outer surface is placed into a body opening for viewing a surgical procedure and a catheter sleeve is wrapped about an endoscope outer surface portion outside the body to attain a sliding relationship along the endoscope surface while the endoscope remains in a viewing position in the body. The catheter sleeve is then moved along the endoscope outer surface to the distal end without disturbing the continuous viewing of the site and the normal endoscope functions. This permits further surgical steps to be achieved without removing and replacing the endoscope including by way of example stapling, retrieving and removing large objects, and tieing off varicose veins.

Having therefore improved the state of the art, those novel features illustrative of the spirit and nature of the invention are defined with particularity in the following claims.

We claim:

1. The endoscopic treatment method comprising the steps of:
   inserting an endoscope with a substantially uniform outer surface into a body opening for viewing,
   wrapping a catheter sleeve carrying at least one lumen for insertion of instruments into the endoscope viewing field about the endoscope outer surface at a position outside the body while the endoscope remains in a viewing position in the body thereby to attain a sliding relationship for moving the catheter sleeve along the endoscope surface to a distal end work site while the endoscope remains in a viewing position in the body, and
   moving the catheter sleeve into the body along the endoscope outer surface to a said distal end work site.

2. The treatment method of claim 1 further comprising the steps of:
provided at least one instrument in said lumen in the catheter sleeve comprising,
stapling means disposed within the lumen during said movement into the body, and
stapling tissue at the distal end of the endoscope with the stapling means while viewing said work site with said endoscope.

3. The treatment method of claim 1 further comprising the steps of:
providing two instruments in said lumen in catheter sleeve respectively for
retaining and removing tissue from said work site,
moving the instruments to the distal end of the endoscope,
removing tissue at the work site with the removing instrument while viewing removal with said endoscope, and
retrieving removed tissue in the tissue retaining means to remove it from the body while the endoscope remains in viewing position within the body.

* * * * *